United States Patent [19]
Sachdeva et al.

[11] Patent Number: 5,683,245
[45] Date of Patent: Nov. 4, 1997

[54] SHAPE MEMORY ORTHODONTIC ARCHWIRE HAVING VARIABLE RECOVERY STRESSES

[75] Inventors: Rohit Chaman Lal Sachdeva, Plano, Tex.; Farrokh Farzin-Nia, Inglewood, Calif.

[73] Assignee: Ormco Corporation, Glendora, Calif.

[21] Appl. No.: 453,160

[22] Filed: May 30, 1995

[51] Int. Cl.$^6$ .................................. A61C 3/00
[52] U.S. Cl. .................................. 433/20; 433/24
[58] Field of Search ........................... 433/20, 24

[56] References Cited

U.S. PATENT DOCUMENTS

| | | |
|---|---|---|
| 4,037,324 | 7/1977 | Andreasen . |
| 4,490,112 | 12/1984 | Tanaka et al. . |
| 4,818,226 | 4/1989 | Berendt et al. . |
| 5,044,947 | 9/1991 | Sachdeva et al. . |
| 5,102,333 | 4/1992 | Suzuki et al. ............ 433/20 X |
| 5,167,499 | 12/1992 | Arndt et al. ............ 433/20 |
| 5,259,760 | 11/1993 | Orikasa ............ 433/20 |
| 5,344,315 | 9/1994 | Hanson ............ 433/20 |

OTHER PUBLICATIONS

"GAC's Low Friction Biological Tooth Movement System" brochure. GAC International, Inc., 185 Oval Drive, Central Islip, New York 11722.

*Primary Examiner*—Nicholas D. Lucchesi
*Attorney, Agent, or Firm*—Wood, Herron & Evans, L.L.P.

[57] ABSTRACT

Orthodontic archwires and methods of making such archwires. The archwire includes a shape memory alloy having a preset shape for exerting forces on teeth during orthodontic treatment. The alloy, which preferably is comprised of at least three elements (e.g., Ni, Ti and Cu), has a transformation temperature ($A_f$) greater than about 25° C., whereby the orthodontic archwire produces forces at normal mouth temperature which are greater than the forces produced at normal room temperature. The orthodontic archwire also preferably has a variable modulus of elasticity.

39 Claims, 2 Drawing Sheets

SHAPE MEMORY ORTHODONTIC ARCHWIRE HAVING VARIABLE RECOVERY STRESSES

FIELD OF THE INVENTION

The invention is directed to orthodontic archwires and, more particularly, to orthodontic archwires employing a shape memory alloy.

BACKGROUND OF THE INVENTION

Traditional systems for the orthodontic treatment of teeth have included the use of a metal orthodontic archwire, such as a stainless steel wire, which is deformed and bent into a particular shape by an orthodontist so as to exert a particular force or forces on orthodontic brackets attached to the teeth. However, such archwires have relatively low shape recovery, and the force applied by the wire varies substantially as the teeth move, requiring frequent archwire adjustment or replacement by the orthodontist. In order to overcome these drawbacks, it has been suggested to use various shape memory alloys.

In U.S. Pat. No. 4,037,324, Andreasen teaches an orthodontic archwire formed of a Nitinol alloy, which exhibits mechanical memory. The Nitinol alloy is a near-stoichiometric alloy of nickel and titanium, preferably having a small amount of cobalt substituted for the nickel on an atom-by-atom basis. Such Nitinol alloys are quite ductile when below a critical temperature (known as transition temperature range) due to martensitic shear, where adjacent planes of atoms shift by a distance less than a full interatomic distance. However, when a Nitinol alloy is heated above its critical temperature, it displays the characteristic of mechanical memory, returning the archwire to its original or pre-deformation shape. Andreasen suggests attaching such an archwire to orthodontic brackets while the archwire is below its critical temperature, and subsequently, heating the wire above its critical temperature to activate the wire memory.

In U.S. Pat. No. 4,490,112, Tanaka et al. teach an orthodontic archwire made of an ultra-elastic material and having a transformation temperature of about 37° C. The ultra-elastic material preferably is a nickel-titanium alloy containing about 50.5 to 51.0 atomic percent nickel, with the balance being titanium. Because the transformation temperature is similar to the normal temperature in the mouth, the orthodontic archwire normally maintains a light orthodontic load on the brackets. However, this load may be increased by increasing the temperature in the mouth.

In U.S. Pat. No. 4,818,226, Berendt et al. disclose an orthodontic archwire formed of a shape memory alloy substantially similar to that taught by the Andreasen '324 patent. The Berendt archwire further includes a first, second, and third curved section, with the first and second curved sections including two different radii of curvature extending distally from the mid-line of the archwire, and a third curved section including two radii of curvature extending distally from the mid-line of the archwire, so that the preset form of the archwire resembles a saddle-like configuration.

In addition, U.S. Pat. No. 5,044,947 to Sachdeva et al. discloses a shape memory orthodontic archwire formed of a nickel-titanium alloy, in which the austenitic transformation temperature ($A_f$) of the alloy may be varied by substituting and/or adding an additional element or elements.

Although the described archwires exhibit shape memory and exert different force levels on orthodontic brackets, depending upon the temperature of the archwire relative to the austenitic transformation temperature of the alloy, the force exerted at any given temperature is substantially the same throughout all regions of the archwire. Therefore, it would also be beneficial to have a shape memory orthodontic archwire which exerts different levels of force (recovery stresses) at different regions of the archwire, when the archwire is in place in the mouth.

SUMMARY OF THE INVENTION

The present invention is directed to an orthodontic archwire and a method of making an archwire. The archwire is comprised of a shape memory alloy having a preset shape for exerting forces on teeth during orthodontic treatment. The alloy has a transformation temperature ($A_f$) greater than about 25° C., such that the orthodontic archwire produces forces at normal mouth temperature which are greater than the forces produced at normal room temperature. A preferred archwire is comprised of an alloy containing at least three elements, each of which is present in an amount greater than or equal to about 2% by weight. Furthermore, the archwires of the invention have at least one curve outside of the normal plane of the archwire. Furthermore, the forces produced by the archwire at normal mouth temperature are at least about ten percent (10%) greater than the forces produced at normal room temperature.

The orthodontic archwire may exhibit variable recovery stresses in selected sections. For example, in one contemplated embodiment, an archwire has a labial section, a plurality of buccal sections, and a plurality of posterior leg sections, with each posterior leg section having a higher modulus of elasticity (and hence greater recovery stress) relative to the buccal sections.

Preferably, the shape memory alloy has a transformation temperature in the range of about 30° C. to about 36° C., and more preferably, about 35° C. The preferred alloy is a nickel-titanium-copper alloy, which may include additional element(s) for the purpose of adjusting and controlling the alloy's transformation temperature. One such element is chromium.

When a nickel/titanium/copper alloy is used, the alloy preferably includes about fifty (50%) percent titanium by weight, about forty-five (45%) percent nickel by weight, and about five (5%) percent copper by weight. If both copper and chromium are included, the alloy preferably includes about fifty (50%) percent titanium by weight, from about 39.5% to about 46.9% nickel by weight, from about three (3%) percent to about ten (10%) percent copper by weight, and from about 0.1% to about 0.5% chromium by weight. More preferably, the alloy having copper and chromium includes about fifty (50%) titanium, from about 42.6% to about 44.85% nickel by weight, from about five (5%) percent to about seven (7%) percent copper by weight, and from about 0.15 to 0.4% chromium by weight.

The orthodontic archwire may be formed in any of a number of preset shapes, including, for example, a reverse curve of spee, which has at least one curve outside of the normal plane of the archwire.

In the method of the invention, an orthodontic archwire comprised of a shape memory alloy is formed into a preselected arch shape, heat treated to provide the desired transformation temperature, and then thermally treated to achieve the desired modulus of elasticity so as to provide necessary stresses. The thermal treatment can be done selectively, i.e., to selected portions of the archwire, to result in an archwire with a variable modulus of elasticity.

Another aspect of the invention concerns a method of orthodontic treatment which includes adhering orthodontic brackets to the teeth and attaching a shape memory orthodontic archwire of the invention to the brackets to achieve the desired corrective tooth movement.

One particular advantage of the orthodontic archwires and methods of treatment of the invention is the ability to provide a shape memory alloy archwire which delivers different levels of force (recovery stresses) to different regions of the maxillary or mandibular arch at a given mouth temperature. Other features, benefits and advantages will become readily apparent to those skilled in the art upon review of the following figures and detailed description of the invention.

DETAILED DESCRIPTION OF THE INVENTION

Figure 1:
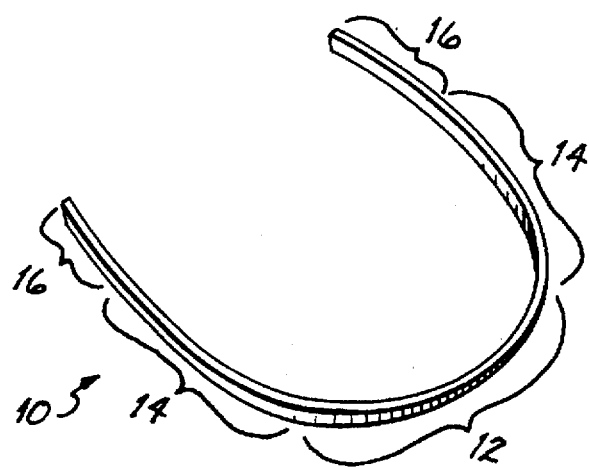
FIG. 1 is a perspective view of an orthodontic archwire having a generally parabolic shape.
Figure 2:
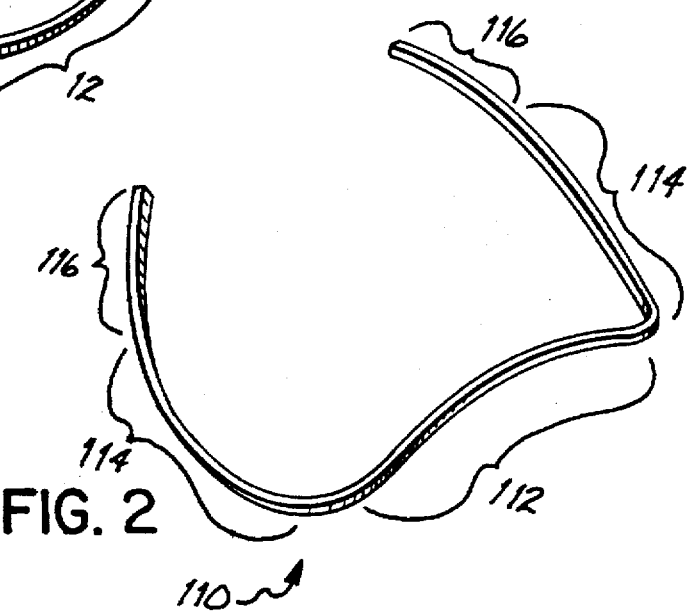
FIG. 2 is a perspective view of an orthodontic archwire having a reverse-curve-of-spee configuration.

The orthodontic archwires of the invention are made by selecting a shape memory alloy having a suitable composition to achieve the desired properties of the archwire, and forming that alloy into a preselected arch shape adapted to exert forces on teeth during orthodontic treatment. If desired, the archwire may be formed into a generally parabolic shape or a reverse-curve-of-spee shape as shown in FIGS. 1 and 2, respectively. However, the shape memory alloy may be formed into any preselected arch shape having utility in orthodontic treatment. Preferably, a nickel-titanium based alloy is used because of its beneficial shape memory characteristics and the ability to modify its physical properties by adjusting the alloy content.

Once the archwire has been formed into a preselected arch shape, such as by work hardening or the like, the archwire is treated to provide the desired austenitic transformation temperature ($A_f$). The desired transformation temperature may be achieved by selecting the appropriate heat treatment, by adjusting the composition of the shape memory alloy, by adjusting the cold work ratio, or by a combination of the above. It is contemplated that a third and even fourth element may be added to the nickel-titanium alloy for the purpose of adjusting and controlling the transformation temperature. Specifically, it is believed that the addition of copper to the Ni—Ti alloy will increase the transformation temperature, while the addition of chromium will reduce the transformation temperature.

Figure 3:
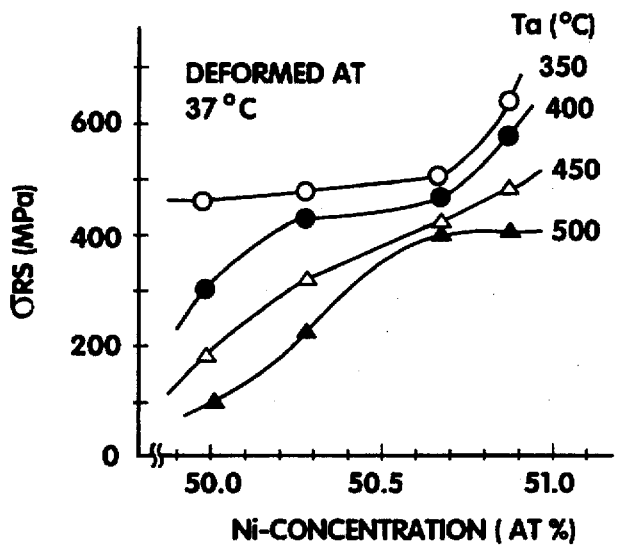
FIG. 3 is a graphical representation of the variation in critical stress for inducing martensite ($\sigma_{MS}$) as a function of Ni concentration.
Figure 4:
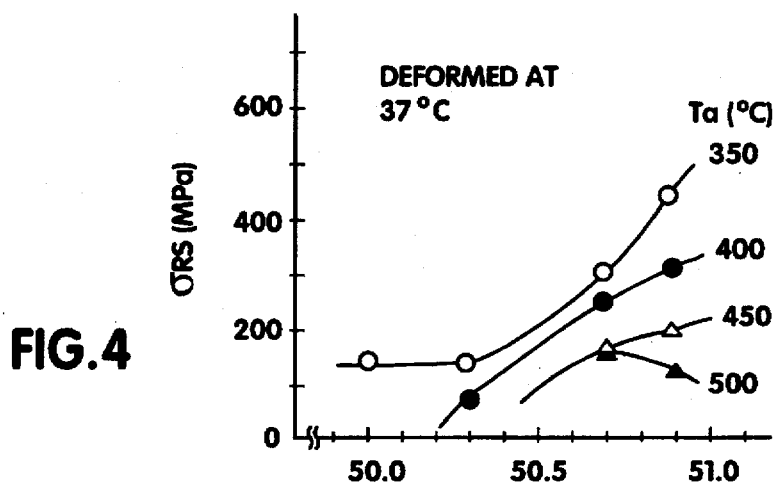
FIG. 4 is a graphical representation of the variation in critical stress for reverse transformation ($\sigma_{RS}$) as a function of Ni concentration.

As shown in Table 1 below, and reflected generally in FIGS. 3 and 4, adjusting the Ni content in a Ni—Ti alloy and adjusting the anneal temperature ($T_a$) of that alloy will change the critical stress for inducing martensite ($\sigma_{MS}$) (see FIG. 3), and the critical stress for reverse transformation ($\sigma_{RS}$) (see FIG. 4). All data given are for a NiTi wire of 0.018" diameter, having the noted composition and annealed at the noted temperature. Also, the stress values in Table 1 were obtained upon deformation at 25° C., whereas the stress values shown in FIGS. 3 and 4 were obtained upon deformation at 37° C.

TABLE 1

| Annealed at 400° C., deformed at 25° C. | | |
|---|---|---|
| NiTi Alloy Ni % | $\sigma_{MS}$ Martensite | $\sigma_{RS}$ Reverse Transformation |
| 50.9 | 500 MPA | 200 MPA |
| 50.7 | 400 MPA | 100 MPA |
| 50.3 | 325 MPA | 75 MPA |
| 50.0 | 200 MPA | 50 MPA |

Orthodontic archwires according to the present invention are formed with a transformation temperature which allows the archwire to produce corrective forces at normal mouth temperature which are greater than the forces produced at normal room temperature. These different levels of force are due to the fact that the shape memory alloy is relatively ductile when below its transformation temperature due to martensitic shear, wherein adjacent planes of atoms shift by a distance less than a full interatomic distance. However, when the archwire is heated above its transformation temperature, the alloy displays its characteristic mechanical memory and attempts to return toward its original preset shape.

As used herein, "normal mouth temperature" refers to the ambient temperature of the mouth without cold or hot foods or liquids present, i.e., a temperature of from about 35° C. to about 38° C. "Normal room temperature" refers to a temperature of from about 18° C. to about 22° C.

The shape memory property of the archwire enables engaging the archwire into the bracket slot by the clinician in a relatively easy manner. Because the transformation temperature of the alloy preferably is at or above normal room temperature, the archwire will readily bend at room temperature and may be connected to the brackets with relative ease. However, as the archwire warms to mouth temperature, the alloy approaches and, depending on the transformation temperature selected, surpasses its transformation temperature, whereby the alloy displays its shape memory characteristic and exerts force (unloading force) on the bracket as the archwire returns to its preselected shape.

Because of the ability to adjust the transformation temperature, it is possible to provide an orthodontic archwire which exerts a relatively mild force, a moderate force, a strong force, or even a pulsing force. For example, if only a mild force is desired, the archwire may be heat treated to provide a transformation temperature relatively close to normal mouth temperature. In this manner, the archwire may be installed relatively easily at room temperature. Then when the archwire reaches normal mouth temperature, it will be in a martensitic/austenitic phase and will exert only a mild shape memory effect. Furthermore, the forces exerted by such an archwire may be pulsed by drinking hot liquids, for example. In a preferred form, the archwire has a transformation temperature of 35° C., in which case a slightly stronger continuous force may be exerted by the archwire on the brackets and teeth when the archwire achieves normal mouth temperature.

Orthodontic archwires of the present invention may also be thermally treated with a controlled heat treatment to provide the desired modulus of elasticity to the archwire. It is contemplated that different sections of the archwire may be subjected to different heat treatments so as to provide a variable modulus of elasticity (and hence variable recovery stresses) along the length of the archwire, which provides a significant advantage. While the force exerted by standard shape memory alloy archwires may be controlled by selecting a particular transformation temperature, the force is relatively uniform along its length. And although such a force may be modified somewhat by various loops and bends in the archwire, these loops or bends may be somewhat unpredictable. However, orthodontic archwires of the present invention are thermally treated, typically by the manufacturer, to provide various moduli of elasticity in different sections of the archwire. Therefore, such archwires may deliver a relatively higher level of force to those portions of the arch requiring more movement, while delivering a lower force to those teeth which require less adjustment.

Figure 5:
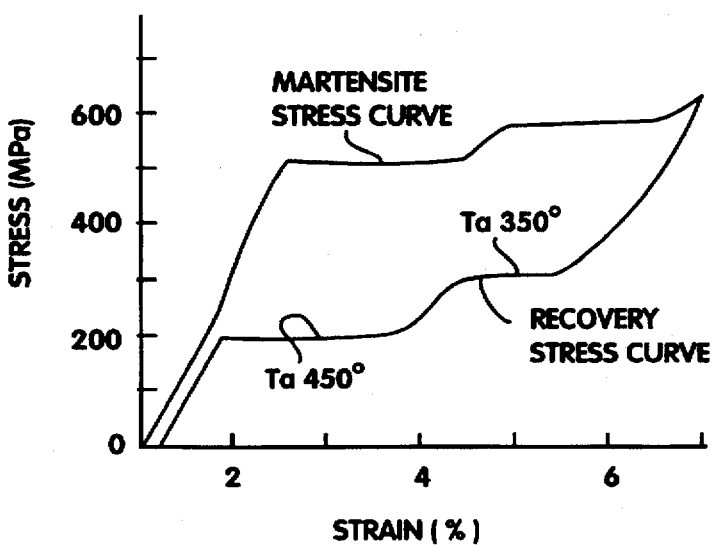
FIG. 5 is a stress-strain curve that shows the effects of differential heat treatment.

Referring to FIGS. 1 and 2, preferred embodiments of the orthodontic archwire 10, 110 are shown including a labial section 12, 112, a plurality of buccal sections 14, 114, and a plurality of posterior leg sections 16, 116. These archwires can be selectively treated to provide a modulus of elasticity which is higher in the posterior leg sections 16, 116 than in the buccal sections 14, 114. With reference to FIG. 5, there is represented, in a graphic manner, the effect of selective heat treatment. The FIG. 5 data is for a Ni—Ti wire (50.6% Ni) of 0.018" diameter wherein a first section was heat treated (annealed) at 450° C., and a second section was heat treated at 350° C. The variation in stress plateaus for inducing martensite and for reverse transformation are apparent at the noted anneal temperatures. Thus it will be appreciated by persons skilled in the art that variable heat treatments of the archwires 10, 110 of the present invention can be advantageously utilized to achieve the desired properties.

While several particular embodiments of the invention have been discussed above, it will be apparent to one of ordinary skill in the art that various other changes and modifications may be made without departing from the scope of the invention, which is determined by the following claims.

What is claimed is:

1. An orthodontic archwire, comprising:
    a shape memory alloy having a preset shape for exerting forces on teeth during orthodontic treatment, said alloy having a transformation temperature ($A_f$) greater than about 25° C., whereby said orthodontic archwire produces forces at normal mouth temperature which are greater than the forces produced at normal room temperature,
    said shape memory alloy comprised of at least three elements, each of which is present in an amount equal to or greater than about 2% by weight;
    said present shape including at least one curve outside of the plane of the archwire; and
    said archwire having a variable modulus of elasticity.

2. The archwire of claim 1 wherein said transformation temperature is in the range of from about 30° C. to about 36° C.

3. The archwire of claim 2 wherein said transformation temperature is about 35° C.

4. The archwire of claim 1 wherein said alloy is a nickel-titanium-copper alloy.

5. The archwire of claim 4 wherein said alloy further includes at least one additional element for the purpose of adjusting and controlling the transformation temperature ($A_f$) of said alloy.

6. The archwire of claim 5 wherein said additional element is chromium.

7. The archwire of claim 6 wherein said alloy comprises about 50% titanium by weight, from about 39.5% to about 46.9% nickel by weight, from about 3% to about 10% copper by weight, and from about 0.1% to about 0.5% chromium by weight.

8. The archwire of claim 7 wherein said alloy comprises about 50% titanium by weight, from about 42.6% to about 44.85% nickel by weight, from about 5% to about 7% copper by weight, and from about 0.15% to about 0.4% chromium by weight.

9. The archwire of claim 4 wherein said alloy comprises about 50% titanium by weight, about 45% nickel by weight and about 5% copper by weight.

10. The archwire of claim 1 wherein said preset shape is a reverse curve of spee.

11. The archwire of claim 1 wherein the forces produced at normal mouth temperature are at least about 10% greater than the forces produced at normal room temperature.

12. The archwire of claim 1 wherein said archwire further includes a labial section, a plurality of buccal sections and a plurality of posterior leg sections, said posterior leg sections having a higher modulus of elasticity than said buccal sections.

13. The archwire of claim 12 wherein said preset shape is a reverse curve of spee.

14. A method of making an improved orthodontic archwire of a shape memory alloy, comprising the steps of:
    forming a shape memory alloy archwire comprised of at least three elements each of which is present in an amount equal to or greater than about 2% by weight into a preselected arch shape for exerting forces on teeth during orthodontic treatment;
    heat treating said archwire to provide it with a transformation temperature ($A_f$) greater than about 25° C., whereby said orthodontic archwire produces corrective forces at normal mouth temperature that are greater than the forces produced at normal room temperature; and
    selectively thermally treating sections of said archwire to provide it with a variable modulus of elasticity.

15. The method of claim 14 wherein said heat treating step provides said archwire with a transformation temperature in the range of from about 30° C. to about 36° C.

16. The method of claim 15 wherein said heat treating step provides said archwire with a transformation temperature of about 35° C.

17. The method of claim 14 wherein said shape memory alloy is a nickel-titanium-copper alloy.

18. The method of claim 17 wherein said alloy further includes an additional element for the purpose of adjusting and controlling the transformation temperature ($A_f$) of said alloy.

19. The method of claim 18 wherein said additional element is chromium.

20. The method of claim 19 wherein said alloy comprises about 50% titanium by weight, from about 39.5% to about 46.9% nickel by weight, from about 3% to about 10% copper by weight, and from about 0.1% to about 0.5% chromium by weight.

21. The method of claim 20 wherein said alloy comprises about 50% titanium by weight, from about 42.6% to about 44.85% nickel by weight, from about 5% to about 7% copper by weight and from about 0.15% to about 0.4% chromium.

22. The method of claim 17 wherein said alloy comprises about 50% titanium by weight, about 45% nickel by weight and about 5% copper by weight.

23. The method of claim 14 wherein said preset shape is a reverse curve of spee.

24. The method of claim 14 wherein the forces produced at normal mouth temperature are at least about 10% greater than the forces produced at normal room temperature.

25. The method of claim 14 wherein said archwire further includes a labial section, a plurality of buccal sections and a plurality of posterior leg sections, said posterior leg sections having a higher modulus of elasticity than said buccal sections.

26. The method of claim 25 wherein said preset shape is a reverse curve of spee.

27. A method of orthodontic treatment, comprising the steps of:

adhering a plurality of orthodontic brackets to a plurality of teeth on a maxillary or mandibular jaw; and attaching an orthodontic archwire to said brackets, said archwire comprising a shape memory alloy comprised of at least three elements, each of which is present in an amount equal to or greater than about 2% by weight, said archwire having a present shape for exerting forces on teeth during orthodontic treatment, said alloy having a transformation temperature ($A_f$) in the range of from about 25° C. to about 45° C., whereby said orthodontic archwire produces forces at normal mouth temperature that are greater than the forces produced at normal room temperature, said archwire further having a variable modulus of elasticity and at least one curve outside the plane of the archwire.

28. The method of claim 27 wherein said transformation temperature is in the range of from about 30° C. to about 36° C.

29. The method of claim 28 wherein said transformation temperature is about 35° C.

30. The method of claim 27 wherein said shape memory alloy is a nickel-titanium-copper alloy.

31. The method of claim 30 wherein said alloy further includes an additional element for the purpose of adjusting and controlling the transformation temperature ($A_f$) of said alloy.

32. The method of claim 31 wherein said additional element is chromium.

33. The method of claim 32 wherein said alloy comprises about 50% titanium by weight, from about 39.5% to about 46.9% nickel by weight, from about 3% to about 10% copper by weight, and from about 0.1% to about 0.5% chromium by weight.

34. The method of claim 33 wherein said alloy comprises about 50% titanium by weight, from about 42.6% to about 44.85% nickel by weight, from about 5% to about 7% copper by weight and from about 0.15% to about 0.4% chromium.

35. The method of claim 30 wherein said alloy comprises about 50% titanium by weight, about 45% nickel by weight and about 5% copper by weight.

36. The method of claim 27 wherein said preset shape is a reverse curve of spee.

37. The method of claim 27 wherein the forces produced at normal mouth temperature are at least about 10% greater than the forces produced at normal room temperature.

38. The method of claim 27 wherein said archwire further includes a labial section, a plurality of buccal sections and a plurality of posterior leg sections, said posterior leg sections having a higher modulus of elasticity than said buccal sections.

39. The method of claim 38 wherein said preset shape is a reverse curve of spee.

* * * * *